United States Patent
Su et al.

(10) Patent No.: US 10,338,064 B2
(45) Date of Patent: Jul. 2, 2019

(54) FULLY-AUTOMATIC IMMUNOFLUORESCENCE QUANTITATIVE ANALYSIS APPARATUS AND DETECTION METHOD

(71) Applicant: GETEIN BIOTECH, INC., Nanjing, Jiangsu (CN)

(72) Inventors: Enben Su, Jiangsu (CN); Weisen Chen, Jiangsu (CN); Lingzhi Yin, Jiangsu (CN); Lin Wang, Jiangsu (CN); Jing Li, Jiangsu (CN); Jing Jin, Jiangsu (CN)

(73) Assignee: GETEIN BIOTECH, INC., Jiangsu (CN)

( * ) Notice: Subject to any disclaimer, the term of this patent is extended or adjusted under 35 U.S.C. 154(b) by 70 days.

(21) Appl. No.: 15/309,083

(22) PCT Filed: May 26, 2015

(86) PCT No.: PCT/CN2015/079758
§ 371 (c)(1),
(2) Date: Nov. 4, 2016

(87) PCT Pub. No.: WO2016/107057
PCT Pub. Date: Jul. 7, 2016

(65) Prior Publication Data
US 2017/0082616 A1  Mar. 23, 2017

(30) Foreign Application Priority Data
Dec. 29, 2014  (CN) .......................... 2014 1 0836485

(51) Int. Cl.
*G01N 35/00* (2006.01)
*G01N 35/10* (2006.01)
(Continued)

(52) U.S. Cl.
CPC . *G01N 33/54366* (2013.01); *G01N 35/00029* (2013.01); *G01N 35/00871* (2013.01);
(Continued)

(58) Field of Classification Search
None
See application file for complete search history.

(56) References Cited

FOREIGN PATENT DOCUMENTS

| CN | 102116771 A | 7/2011 |
|----|-------------|--------|
| CN | 102998473 A | 3/2013 |

(Continued)

OTHER PUBLICATIONS

Sep. 15, 2015 International Search Report issued in International Patent Application No. PCT/CN2015/079758.

*Primary Examiner* — Kathryn Wright
(74) *Attorney, Agent, or Firm* — Oliff PLC

(57) ABSTRACT

A fully-automatic immunofluorescence quantitative analyzing apparatus and detection method belong to the field of quantitative immunofluorescence analysis and detection. The immunity quantitative analyzing apparatus includes a support baseplate, a reagent strip storage and automatic loading module, a cuvette ring module, a detection module, a sample module, a sample dispensing module, a washing module and a control system, the reagent strip storage and automatic loading module, the cuvette ring module, the detection module, the sample module, the sample dispensing module, the washing module being sequentially arranged on the support baseplate. The reagent strip storage and automatic loading module provides a reagent strip for the cuvette ring module, and the sample dispensing module dispenses the sample on the sample module to the cuvette ring module and performs a reaction, and the sample enters the detection module to complete the detection after the reaction is complete.

18 Claims, 7 Drawing Sheets

(51) Int. Cl.
*G01N 33/543* (2006.01)
*G01N 35/02* (2006.01)
*G01N 35/04* (2006.01)

(52) U.S. Cl.
CPC ........... *G01N 35/025* (2013.01); *G01N 35/04* (2013.01); *G01N 35/1011* (2013.01); *G01N 2035/00108* (2013.01); *G01N 2035/00326* (2013.01); *G01N 2035/0444* (2013.01); *G01N 2035/0465* (2013.01); *G01N 2035/0484* (2013.01); *G01N 2035/0498* (2013.01); *G01N 2035/103* (2013.01)

(56) References Cited

FOREIGN PATENT DOCUMENTS

| | | |
|---|---|---|
| CN | 203337661 U | 12/2013 |
| CN | 103592450 A | 2/2014 |
| CN | 104535782 A | 4/2015 |
| CN | 204347046 U | 5/2015 |
| EP | 0 497 019 A1 | 8/1992 |

A reagent strip storage and automatic loading module loads a reagent strip to enter a reagent strip inserting slot of the reaction disc

A cuvette ring starts to rotate, the reagent strip in a first position enters a sample dispensing region along with rotation and is paused, a sample in the sample module is sucked by the sample dispensing module to dispense into a reagent strip sample dispensing opening, and immunofluorescence reaction starts

The cuvette ring continuously rotates, the reagent strip in the first position gets away from the sample dispensing region, and the reagent strips in the subsequent position enter the sample dispensing region one after another, and are paused one by one, thus finishing sample dispensing

The cuvette ring continuously rotates, the reagent strip in the first position rotates to the detection module and is paused, and the detection device finishes the detection on the reagent strip in the first position and sends a result to a computer for processing

FIG. 13

FULLY-AUTOMATIC IMMUNOFLUORESCENCE QUANTITATIVE ANALYSIS APPARATUS AND DETECTION METHOD

BACKGROUND

Technical Field

The present invention belongs to the field of quantitative immunofluorescence analysis and detection, and in particular relates to a fully-automatic immunofluorescence quantitative analyzing apparatus and detection method.

Related Art

POCT (point-of-care testing) is a subdivisional industry of in vitro diagnostic (IVD) instruments, i.e., sampling is performed on site for instant analysis, a complex procedure of laboratory inspection of a sample is omitted, and an inspection result is rapidly obtained.

When immunofluorescence quantitative detection is performed, most diagnostic instruments on the market at present are semi-automatic detection instruments, for example, the existing immunofluorescence chromatography analyzer GP1100 of Nanjing Getein Biotech, Ltd., is a semi-automatic detection instrument, its machine structure only comprises a light path system and an electronic display system for quantitative detection, and the sample dispensing and chromatography processes are performed manually outside the machine; in use, firstly, sample dispensing is performed outdoor by the semi-automatic instrument, which is very unfavorable for product instruction with very high demands on temperature; secondly, since the manual sampling and sample dispensing steps are required, and then quantitative analysis is performed by the instrument, a test error generated by manual intervention is increased, immunochromatography extending time and a sample dispensing precision are inaccurate, a test speed is slow, and manual sample dispensing easily causes biological contamination; finally, the existing small sized detection instruments can only load one sample at one time, and another sample is dispensed thereinto after the detection is complete. As a result, the following defects are caused: special attending labor is necessary, the loaded sample is operated repeatedly, the biological contamination is caused by manual intervention, and meanwhile, detection personal cannot leave for performing other detection works; in addition, one sample is detected at one time, the efficiency is low, and illness state diagnosis is delayed; and outdoor sample dispensing is unsuitable for the production detection with high temperature demands.

SUMMARY

In order to overcome the defects of the prior art, the present invention discloses a fully-automatic immunofluorescence quantitative analyzing apparatus and detection method, and the device can repeatedly continuously perform immunofluorescence quantitative detection work, and is high in sensitivity, simple and convenient to operate and high in repeatability.

The present invention adopts the following technical solution: the fully-automatic immunofluorescence quantitative analyzing apparatus comprises a support baseplate, a reagent strip storage and automatic loading module, a cuvette ring module, a detection module, a sample module, a sample dispensing module, a washing module and a control system, wherein the reagent strip storage and automatic loading module, the cuvette ring module, the detection module, the sample module, the sample dispensing module and the washing module are sequentially arranged on the support baseplate. The reagent strip storage and automatic loading module provides a reagent strip for the cuvette ring module, and the sample dispensing module dispenses the sample in the sample module to the v module and performs a reaction, and the sample enters the detection module to complete the detection after the reaction is complete.

The sample dispensing module comprises an XYZ motion mechanical arm, a disposable tip detector and a diluter pump; the XYZ motion mechanism arm comprises an X arm, a Y arm and a Z arm, and the X arm is horizontally disposed along the sample module and the cuvette ring module; the Y arm is located on the upper part of the sample module, is vertically connected to the X arm and can slide on the X arm; the Z arm is vertically fixed in a chute of the Y arm and can slide front and back and up and down along the Y arm, and the bottom of the Z arm is provided with the disposable tip detector. The X arm, the Y arm and Z arm are all connected to a stepmotor assembly, the control system controls the stepmotor assembly to control the Y arm and Z arm to slide, such that the disposable tip detector can move up and down and left and right in regions of the sample module and the cuvette ring module.

The sample module comprises a disposable tip box, a mixing box, a diluent slot, a sample unit, a tip collection box and a sample module box; the sample unit and the diluent slot are located on a bottom plate of the sample module box, the bottom plate is provided with a track, the bottoms of the sample unit and the diluent slot are provided with a clamping slot matched with the track, and the sample unit and the diluent slot slide front and back on the track of the bottom plate; one side of the sample module box is provided with a platform, the lower part of which is spaced from the ground, the tip collection box, the disposable tip box and the mixing box are arrayed on the platform, part of the tip collection box penetrates through the platform, on the platform, the other part of the tip collection box is in the spacing space of the lower part of the platform, the top end of the tip collection box is provided with a recycling opening, the bottom end of the tip collection box is not sealed, the sucker directly falls onto the bottom plate after entering the recycling opening, and the disposable tip box and the mixing box are supported by the support frame.

The sample module box is set to be a drawer shape, baffles are disposed on two sides, pulleys are disposed outside the baffles and can slide front and back along outside slideways, and the front ends of the baffles are provided with fixed bolts for fixing the drawer.

The cuvette ring module is a disc-like device, reagent strip inserting slots are fixed on the edge of the disc, and inserting slot openings correspond to a reagent strip outlet of the reagent strip storage and automatic loading module in position to load the reagent strip; the cuvette ring brings the reagent strip to the position corresponding to the sample dispensing module to finish the sample dispensing operation; the cuvette ring brings the reagent strip to the position corresponding to the detection module to finish detection operation.

The cuvette ring is connected to a first motor, and the first motor drives the cuvette ring to rotate by driving a first timing pulley and a first timing belt; a number of the cuvette ring reagent strip inserting slots is 2N or 2N+1, N is larger than or equal to 1, and the number of the reagent strip inserting slots is preferably 16-20, and more preferably 16.

The reagent storage and automatic loading module comprises a reagent strip storage box, a storage box bracket and an automatic loading assembly, the storage box bracket is fixed on the support baseplate, and the reagent strip storage box is fixed on the storage box bracket by a padlock; the automatic loading assembly consists of a second motor, a second timing pulley, a second timing belt and an elastic hanging rod; the control system controls the second motor to operate and drives the second timing pulley, the second timing belt and the elastic hanging rod to move. A reagent strip inserting slot is disposed in the cuvette ring module, the middle of the lower bottom surface is provided with a notch, and the notch allows the elastic hanging rod to feed the reagent strip to enter the reagent strip inserting slot. The elastic hanging rod is a rodlike object, is located below the reagent strip inserting slot of the reaction disc, and can reciprocate under the cuvette ring and the storage box along the straight line, i.e., the inserting slot, and its front end rod part is provided with an elastic hook capable of being pressed down. During working, the hook enters to be under the reagent strip, is pressed down by the reagent strip till the reagent strip enters a groove below the reagent strip to be restored, and reciprocates to bring the reagent strip from the storage box till the reagent strip enters the reagent disc inserting slot of the reaction disc, and when quitting, the hook is repressed down to quit the reagent strip groove.

The reagent strip storage box comprises a box body and a box cover part, which are sealed; a reagent strip lowering guide rail is in the reagent strip storage box; the bottom of the reagent strip storage box is provided with a notch, and a sealing elastic piece is disposed on the bottom end of the side surface of the reagent strip storage box close to the notch; the notch extends from one side of the bottom end to the other side of the reagent strip storage box, and its extending strength can just correspond to the reagent strip slot opening to the other side of the bottom end, and the sealing elastic piece can be only elastic toward the outside of the reagent strip storage box.

1-3 reagent strip storage and automatic loading modules are disposed.

Drying agent inserting holes for placing the drying agents are disposed on the peripheral walls of the reagent strip storage box.

The reagent strip lowering guide rail can be a guide rail attached to the inner wall of the body of the reagent strip storage box or a guide rail suspended from the top, and the distance between the reagent strip lowering guide rail and the bottom end of the reagent strip storage box is between the thicknesses of 1-2 reagent strips.

The reagent strip storage box bracket assembly is provided with a sensor, through which the residual number of the reagent strips is counted.

The detection module is disposed on the support baseplate, and is located around the reaction disc, such that the reagent strips in the cuvette ring can be detected thereunder. The detection module comprises an optical detection device, and the reagent strips in the cuvette ring are rotated to be under the detection device to finish the fluorescence detection.

The bottom of the detection module is provided with an elastic hanging rod, after finishing the detection of the reagent strip, the elastic hanging rod under the detection module pushes the reagent strip out of reaction disc, and the reagent strip enters to be under the detection device. After the detection of the next reagent strip is finished, the last reagent strip is pushed out of the device of the present embodiment by the next reagent strip, and the next reagent strips stays under the detection device. The elastic hanging rod on the bottom of the detection module is same as the elastic hanging rod mechanism under the reagent agent inserting slot of the cuvette ring in principle.

The washing module comprises a probe washing slot, a waste liquid bottle and a washing liquid bottle, wherein a catheter in the probe washing slot is connected to the waste liquid bottle and the washing liquid bottle. After sample dispensing is finished, the disposable tip detector moves to the probe washing slot, washing liquid in the washing liquid bottle washes the disposable tip detector, and waste liquid flows into the waste liquid bottle by a pipeline.

Another objective of the present invention is to provide a fully-automatic immunofluorescence quantitative analysis detection method, comprising the following steps:

step 1: a reagent strip storage and automatic loading module loads a reagent strip to enter a reagent strip inserting slot of the reaction disc;

step 2: a cuvette ring starts to rotate, the reagent strip in a first position enters a sample dispensing region along with rotation and is paused, a sample in the sample module is sucked by the sample dispensing module to dispense into a reagent strip sample dispensing opening, and immunofluorescence reaction starts;

step 3: the cuvette ring continuously rotates, the reagent strip in the first position gets away from the sample dispensing region, and the reagent strips in the subsequent position enter the sample dispensing region one after another, and are paused one by one, thus finishing sample dispensing;

step 4: the cuvette ring continuously rotates, the reagent strip in the first position rotates to the detection module and is paused, and the detection device finishes the detection on the reagent strip in the first position and sends a result to a computer for processing.

The sample dispensing step comprises the following conditions:

A: condition in which the sample needs no diluting: the sample dispensing device firstly picks a disposable sucker, then moves to a sample region to suck the sample, then moves to a cuvette ring region to finish a sample dispensing process, then moves to the recycling opening of a disposable tip collection box to remove the disposable sucker, and then performs a new round of sample dispensing;

B: the condition which the sample needs to be diluted: the sample dispensing device firstly picks the disposable sucker, moves to the sample region to suck the sample, then moves to a diluent slot to dispense the sample into the diluent slot, then sucks diluent to inject, repeatedly pumps in and out to dilute the sample, then moves to the cuvette ring sample dispensing region to finish the sample dispensing, then recycles the disposable sucker, and then moves to a disposable tip box to pick a new sucker for a new round of sample dispensing.

Various samples are arrayed in the sample module.

The present invention has the beneficial effects:

the fully-automatic immunofluorescence quantitative analyzing apparatus provided by the present invention addresses the problem that it is difficult to automate an in vitro diagnostic product, cross contamination is avoided by the disposable sample sucking device, reaction time is precise to control, repeatability and test accuracy of the instrument are improved, automatic test of the fast diagnostic instrument is realized, manual errors are reduced, test precision is improved and test efficiency is improved.

The present invention can detect a plurality of samples together and is also suitable for direct sample dispensing detection and the detection in which the sample needs to be diluted.

The drying holes are dispensed in the reagent strip storage box of the present invention, the dryness of the reagent strip is ensured and detection accuracy is improved.

The present invention contains a liquid path probe washing system and can ensure cleanliness of the disposable tip detector, such that the sucked samples are not contaminated.

BRIEF DESCRIPTION OF THE DRAWINGS

FIG. 13 is a flow schematic diagram of a fully-automatic immunofluorescence quantitative analysis method.

Figure 1:
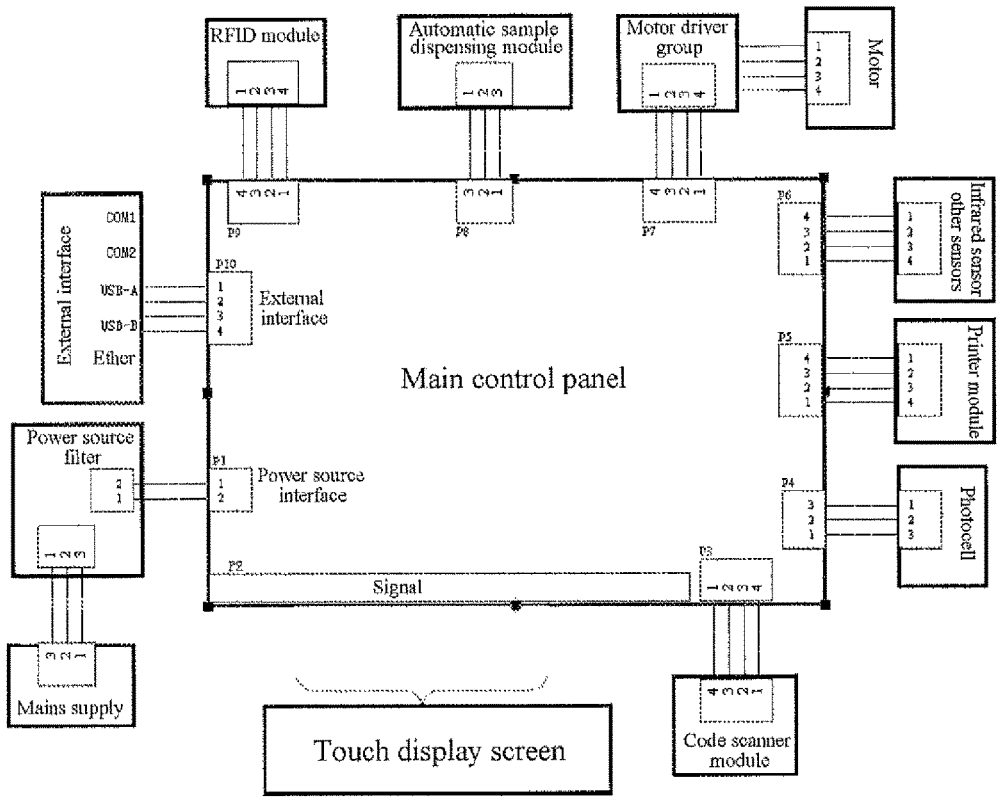
FIG. 1 is a structural schematic diagram of a control system of a fully-automatic immunofluorescence quantitative analyzing apparatus.

In the drawings: 1 is support baseplate, 2 is circuit box, 3 is reagent strip storage and automatic loading module, 4 is cuvette ring module, 5 is detection module, 6 is sample module, 7 is sample dispensing module, 8 is washing module, 9 is X arm, 10 is Y arm, 11 is Z arm, 12 is disposable tip detector, 13 is stepmotor assembly, 14 is pulley, 15 is slideway, 16 is fixed bolt, 17 is disposable tip box, 18 is mixing box, 19 is diluent box, 20 is sample unit, 21 is tip collection box, 22 is track, 23 is platform, 24 is recycling opening, 25 is bracket, 26 is reagent strip inserting slot, 27 is reagent strip outlet, 28 is reagent strip inserting slot notch, 29 is first motor, 30 is first timing pulley, 31 is first timing belt, 32 is reagent strip storage box, 33 is storage box bracket, 34 is padlock, 35 is second motor, 36 is second timing pulley, 37 is second timing belt, 38 is elastic hanging rod, 39 is optical detection device, 40 is front box plate, 41 is probe washing slot, 42 is diluter pump, 43 is washing liquid bottle, 44 is waste liquid bottle, 45 is automatic loading assembly, 46 is reagent strip lowering guide rail, 47 is notch, 48 is sealing elastic piece, 49 is drying agent inserting hole, 50 is sensor and 51 is reagent strip track.

DETAILED DESCRIPTION

The fully-automatic immunofluorescence quantitative analyzing apparatus and detection method are described in detail in combination with drawings.

Embodiment 1

Figure 2:
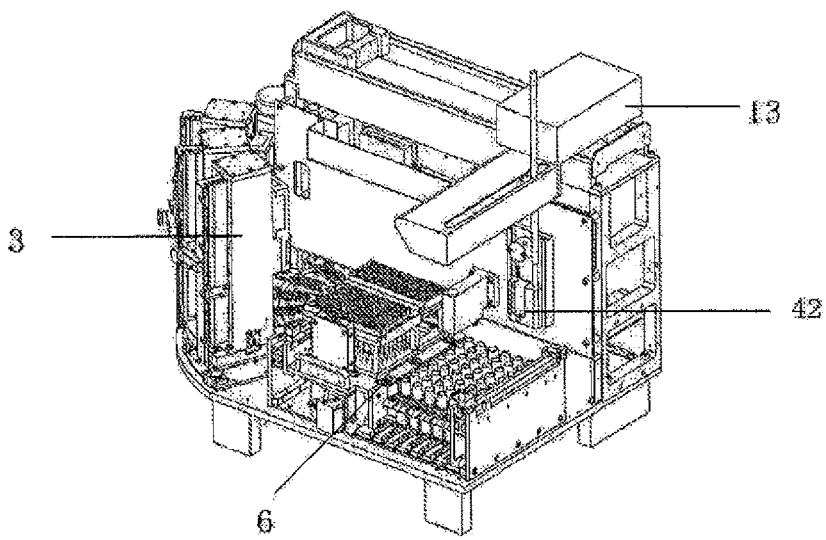
FIG. 2 is a space diagram of a fully-automatic immunofluorescence quantitative analyzing apparatus.
Figure 3:
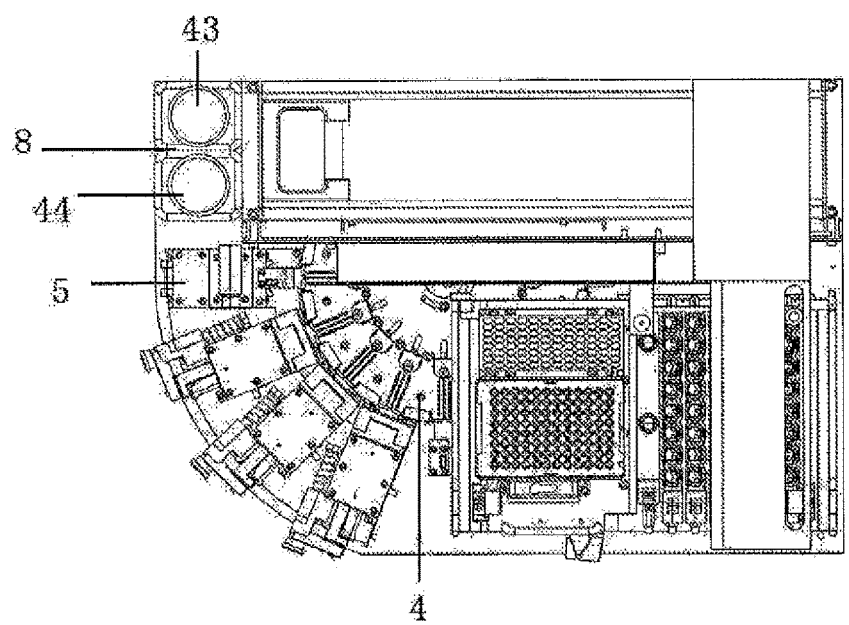
FIG. 3 is a top view of a fully-automatic immunofluorescence quantitative analyzing apparatus.
Figure 4:
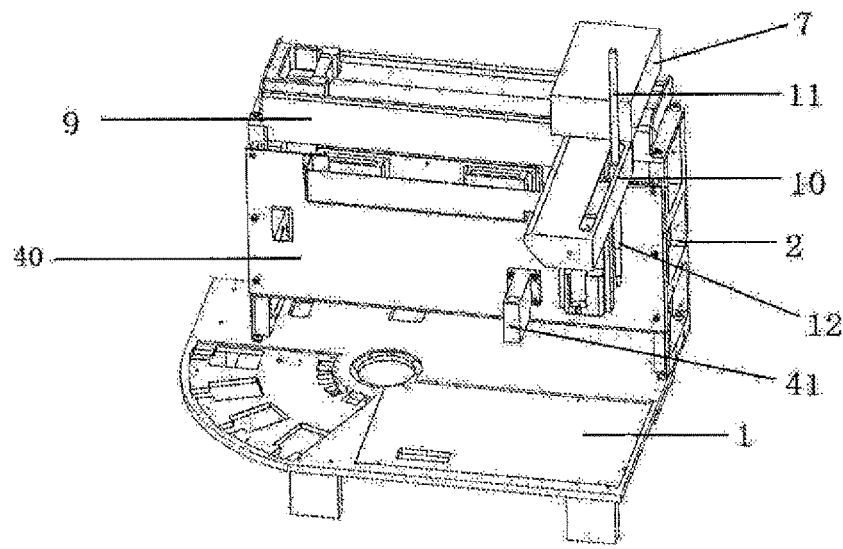
FIG. 4 is a structural schematic diagram of a bracket of a fully-automatic immunofluorescence quantitative analyzing apparatus.

As shown in FIG. 2, FIG. 3, and FIG. 4, a fully-automatic immunofluorescence quantitative analyzing apparatus comprises a support baseplate 1 and a control system and also comprises a reagent strip storage and automatic loading module 3, a cuvette ring module 4, a detection module 5, a sample module 6, a sample dispensing module 7, a washing module 8, which are sequentially arranged on the support baseplate; the reagent strip storage and automatic loading module 3 provides a reagent strip for the cuvette ring module 4, and the sample dispensing module 7 dispenses the sample in the sample module 6 to the cuvette ring module 4 and performs a reaction, and the sample enters the detection module 5 to complete the detection after the reaction is complete.

As shown in FIGS. 2 and 4, the sample dispensing module 7 comprises an XYZ motion mechanical arm and a disposable tip detector 12; an X arm 9 is horizontally disposed and can be located at the top end of a circuit box 2, a Y arm 10 is located on the upper part of the sample module 6, is vertically connected to the X arm 9 and can slide on the X arm 9; a Z arm 11 is vertically fixed in a chute of the Y arm 10 and can slide front and back and up and down along the Y arm 10, the bottom of the Z arm 11 is provided with the disposable tip detector 12, the X, Y and Z arms are all connected to a stepmotor assembly 13, and the stepmotor assemblies 13 are controlled by the system and can control the Y arm and Z arm to slide, such that the disposable tip detector 12 can move up and down and left and right in regions of the sample module 6 and the cuvette ring module 4. The circuit box 2 a circuit, a main control board and various control devices.

Figure 5:
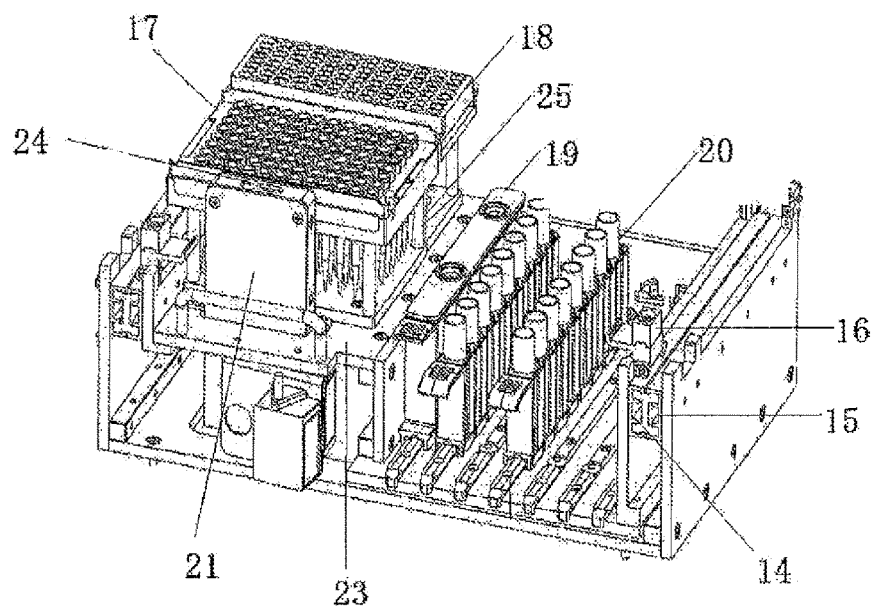
FIG. 5 is a structural schematic diagram of a sample module.

As shown in FIG. 5, the sample module 6 is a drawer-like device, baffles are disposed on left and right sides, pulleys 14 are disposed outside the baffles and can slide front and back along outside slideways 15, and the front ends of the baffles are provided with fixed bolts 16 for fixing the drawer; the sample module 6 comprises a disposable tip box 17, a mixing box 18, a diluent slot 19, a sample unit 20 and a tip collection box 21; the sample unit 20 is located on a bottom plate of the sample module box, is fixed by a track 22 on the bottom plate and can be drawn out by sliding front and back; the drawer is provided with a platform 23, the lower part of which is spaced from the ground, the tip collection box 21, the disposable tip box 17 and the mixing box 18 are arrayed on the platform 23 in sequence, part of the tip collection box 21 penetrates through the platform 23, on the platform 23, the other part of the tip collection box is under the platform 23, the top end of the tip collection box 21 is provided with a recycling opening 24, the bottom end is hollow, the sucker directly falls onto the bottom plate after entering the recycling opening 24, and the disposable tip box 17 and the mixing box 18 are supported by the bracket 25. The diluent slot is located between the sample unit 20 and the platform 23, and is fixed on the bottom plate by the bottom plate track 22.

Figure 6:
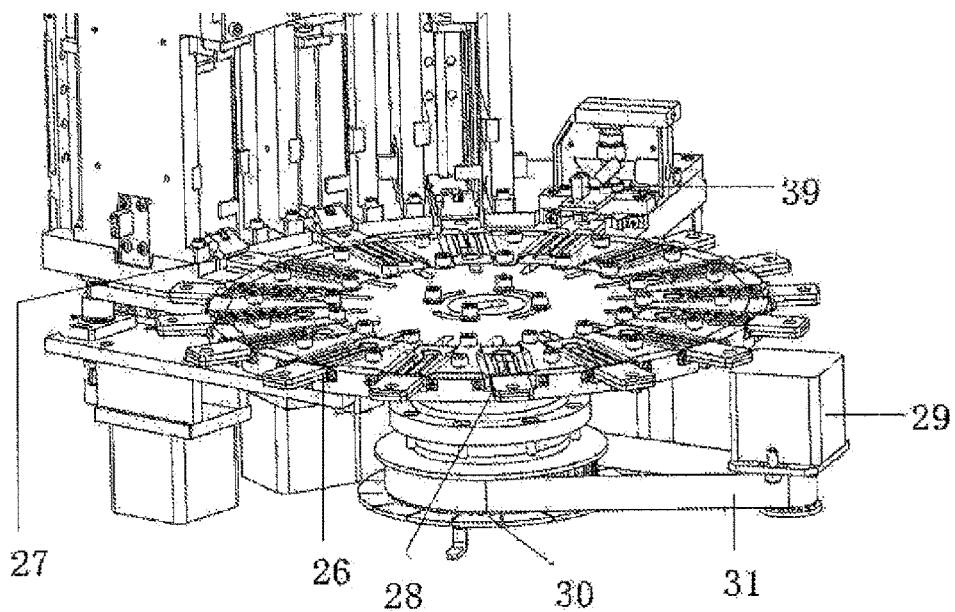
FIG. 6 is a structural schematic diagram of a cuvette ring module.

As shown in FIG. 6, the cuvette ring module 4 is a disc-like device, 16-20 reagent strip inserting slots 26 are fixed on the edge of the disc, and inserting slot openings correspond to a reagent strip outlet 27 of the reagent strip storage and automatic loading module 3 in position; the reagent strip storage and automatic loading module 3 can push the reagent strip into the reagent strip inserting slot 26; the lower part of the cuvette ring module 4 penetrates through the bottom plate and is connected to a first motor 29 on the bottom of the bottom plate, the first motor 29 is connected to the control system, and the control system drives the first timing pulley 30 and the first timing belt 31 by regulating the first motor 29 and finally drives the rotation of the reaction disc.

As shown in FIGS. 3 and 6, the detection module 5 is located between the reagent strip storage and automatic loading device 3 and the circuit box 2, an immunofluorescence detection device 39 is disposed on the detection module, and the reagent strip in the cuvette ring rotates to be under the detection device to finish the fluorescence detection.

As shown in FIGS. 2, 3 and 4, the circuit box 2 is fixed on the baseplate 1 and comprises a box top, a front box plate 40, a rear box plate and a side box plate, wherein the front box plate is provided with a probe washing slot 41, in which a catheter is located and is connected to a waste liquid bottle 44 and a washing liquid bottle 43 located outside the side box plate; the front box plate is also provided with a diluter pump 42, connected to the disposable tip detector 12.

The device of the present invention also comprises a corresponding information output module, for example, an external computer, a printer and a touch display screen.

As shown in FIG. 1, a control system of the fully-automatic immunofluorescence quantitative analyzing apparatus comprises a power source interface (P1), a main control panel, a touch display screen, an external interface (P10) and RFID module, a code scanner module, a printer module, a photocell signal input, a motor driver group, a motor, an automatic sample dispensing module, an infrared sensor and other sensors; the mains supply from the power source interface is subjected to noise filtering by a power source filter, is then converted into a 24V direct current power source by a switch power source, and is provided for the main control panel and related modules. The main control panel is an instrument control center, loads a main control program, collects the information of each path sensor, and receives operation requests through each input interface, the instrument is manipulated to operate a detection test and manage an instrument state according to an output control instrument precompiled by a software system and a method document, corresponding information is output to an external computer, printer and touch display screen by the output device; the automatic sample dispensing module operates each pump and mechanical arm of a liquid path system according to an instruction of the main control panel; a photocell and other sensors provide necessary information; the external interface panel provides an interface to be connected to an external computer, an external code scanner and inputs and outputs information.

In the present embodiment, a working principle of the fully-automatic immunofluorescence quantitative analyzing apparatus is as follows: the fully-automatic immunofluorescence quantitative analyzing apparatus moves to the sample module 6 by the XZY motion mechanical arm of the sample dispensing module 7, and picks a disposable sucker from the disposable tip box 17 by a disposable tip detector 12 of the Z arm 11, the mechanical arm moves a sample to be above the sample unit 20, the diluter pump 42 sucks the sample in a sample tube by the disposable sucker through the up and down moving of the Z arm 11, after sucking, the instrument selects whether to dilute according to different test projects, if there is no diluting, the XYZ mechanical arm directly sucks the disposable sucker to the reagent strip in the position of the cuvette ring reagent strip inserting slot 26, the reagent strip with the sample finishes the reaction on the reaction disc, after the reaction is complete, the reagent strip rotates to the detection module 5 and is detected by the optical detection device 39, and is then pushed out of the instrument; if the sample needs to be diluted, the XYZ mechanical arm injects the sample sucked by the disposable sucker into the diluent slot 19 and sucks proper amount of diluent and injects into the diluent slot 19, through the repeated pumping in and out of the diluter pump 42, the sample and the diluent are fully mixed, the XYZ motion mechanical arm conveys the disposable sucker to the reagent strip in the position of the cuvette ring reagent strip inserting slot 26, the reagent strip with the sample finishes the reaction on the reaction disc, after the reaction is complete, the reagent strip rotates to the detection module 5 and is detected by the optical detection device 39, and is then pushed out of the instrument.

After the sample dispensing is finished, the disposable tip detector 12 moves to the probe washing slot 41, the washing liquid in the washing liquid bottle 44 cleans the disposable tip detector 12 and waste liquid flows into the waste liquid bottle 43 by a pipeline.

Embodiment 2

According to the fully-automatic immunofluorescence quantitative analyzing apparatus, specific structures of the reagent strip storage and automatic loading module 3 and the matched cuvette ring module 4 are as follows, and other modules are structured similar to those of embodiment 1.

Figure 7:
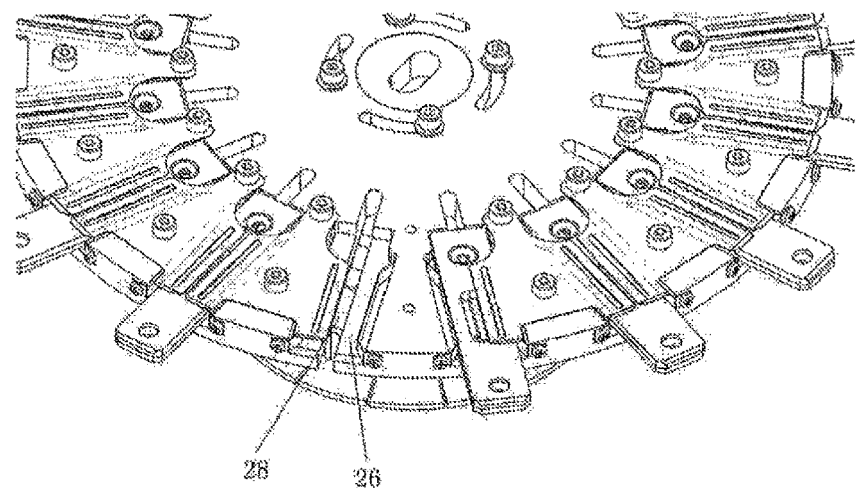
FIG. 7 is a memory structural schematic diagram of a cuvette ring without a reagent strip.

As shown in FIG. 6, the cuvette ring module 4 is a disc-like device, reagent strip inserting slots 26 are fixed on the edge of the disc, and inserting slot openings correspond to a reagent strip outlet 27 in position, as shown in FIG. 7, the middle of the lower bottom surface of the reagent strip inserting slot 26 is provided with a notch 28, and the notch 28 allows an elastic hanging rod 38 to feed the reagent strip to enter the reagent strip inserting slot 26; the lower part of the cuvette ring module 4 penetrates through the bottom plate and is connected to a first motor 29 on the bottom of the bottom plate, the first motor 29 is connected to the control system, and the control system drives the first timing pulley 30 and the first timing belt 31 by regulating the first motor 29 and finally drives the rotation of the reaction disc.

Figure 8:
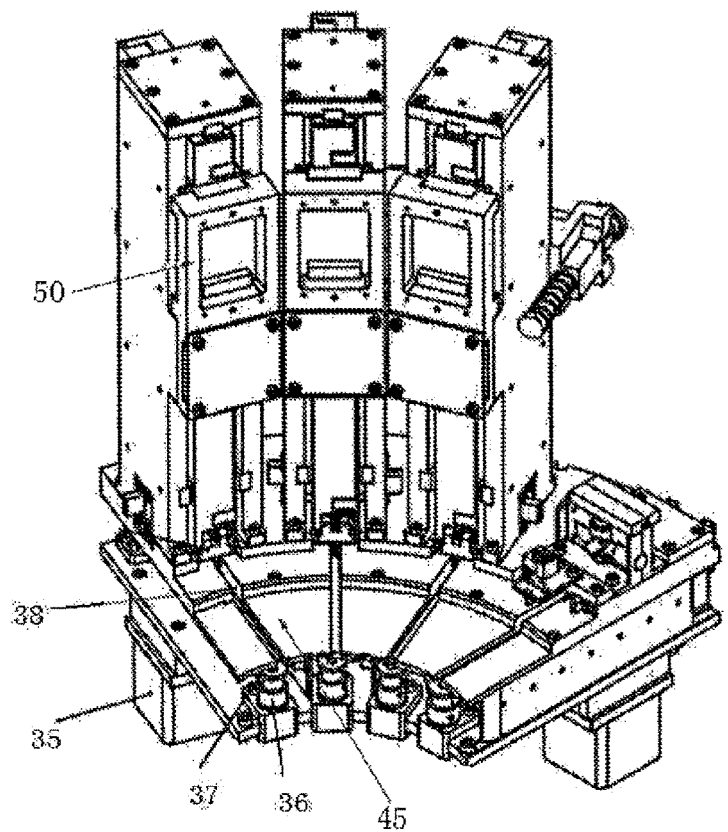
FIG. 8 is a structural schematic diagram of a reagent strip storage and automatic loading module.
Figure 9:
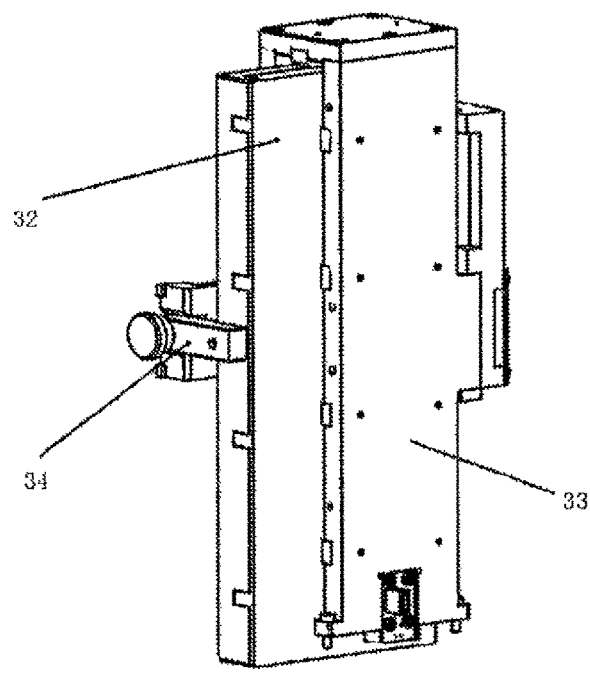
FIG. 9 is a structural schematic diagram of a reagent strip storage box and a bracket assembly.
Figure 12:
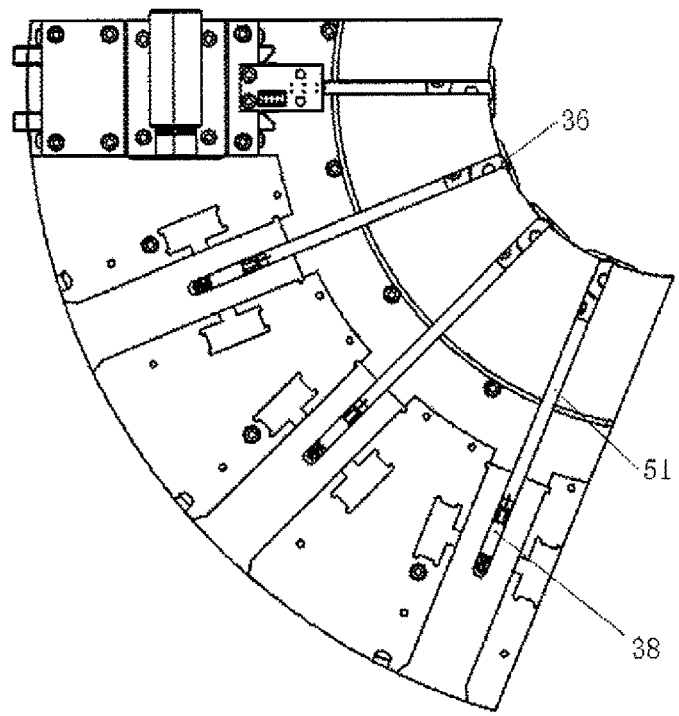
FIG. 12 is structural schematic diagram of an automatic popping out device of a reagent strip storage box.

As shown in FIG. 8 and FIG. 9, the reagent strip storage and automatic loading module 3 comprises a reagent strip storage box 32, a storage box bracket 33 and an automatic loading assembly 45, the storage box bracket 33 is fixed on the support baseplate 1, and the reagent strip storage box 32 is fixed on the storage box bracket 33 by a padlock 34; the automatic loading assembly 45 consists of a second motor 35, a second timing pulley 36, a second timing belt 37 and an elastic hanging rod 38; the control system controls the second motor 35 to operate and drives the second timing pulley 36, the second timing belt 37 and the elastic hanging rod 38 to move so as to hook out the reagent strip on the bottom of the reagent strip storage box 32 and feed the reagent strip into the reagent strip inserting slot 26 of the reaction disc. As shown in FIG. 12, the elastic hanging rod 38 is a rodlike object, is located below the reagent strip inserting slot 26 of the reaction disc, and can reciprocate under the cuvette ring and the storage box along the straight line, i.e., the inserting slot. The front end rod part of the elastic hanging rod 38 is provided with an elastic hook capable of being pressed down. During working, the hook enters to be under the reagent strip, is pressed down by the reagent strip till the reagent strip enters a groove below the reagent strip to be restored, and reciprocates to bring the reagent strip from the storage box till the reagent strip enters the reagent disc inserting slot of the reaction disc, and when quitting, the hook is repressed down to quit the reagent strip groove.

The reagent strip storage box 32 comprises a box body and a box cover part, which are sealed by a manner of inserting slot or screws; a reagent strip lowering guide rail 46 is in the reagent strip storage box 32; the bottom of the reagent strip storage box 32 is provided with a notch 47, and a sealing elastic piece 48 is disposed on the bottom end of the side surface of the reagent strip storage box 32 close to the notch 47; drying agent inserting holes 49 for placing a drying agent are disposed in the peripheral wall of the reagent strip storage box 32.

Figure 10:
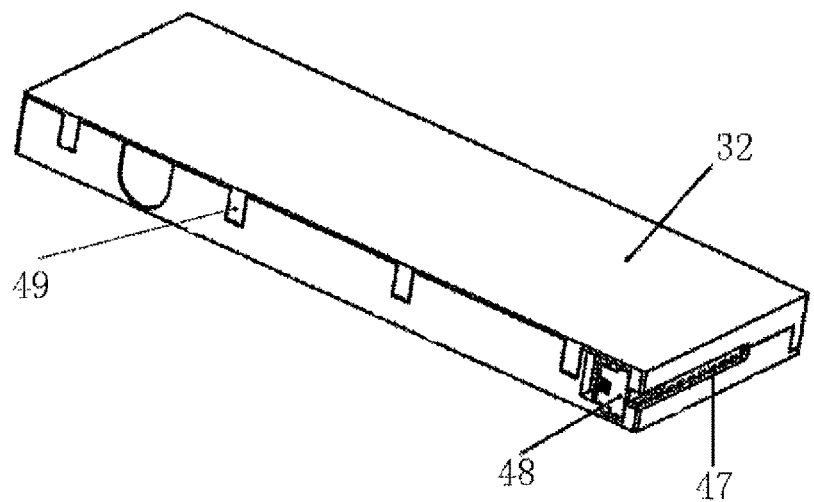
FIG. 10 is an external structural schematic diagram of a reagent strip storage box.

As shown in FIG. 10, the notch 47 extends from one side of the bottom end to the other side of the reagent strip storage box 32, and its extending strength can just correspond to the reagent strip slot opening to the other side of the bottom end, and the sealing elastic piece 48 can be only elastic toward the outside of the reagent strip storage box 32.

Figure 11:
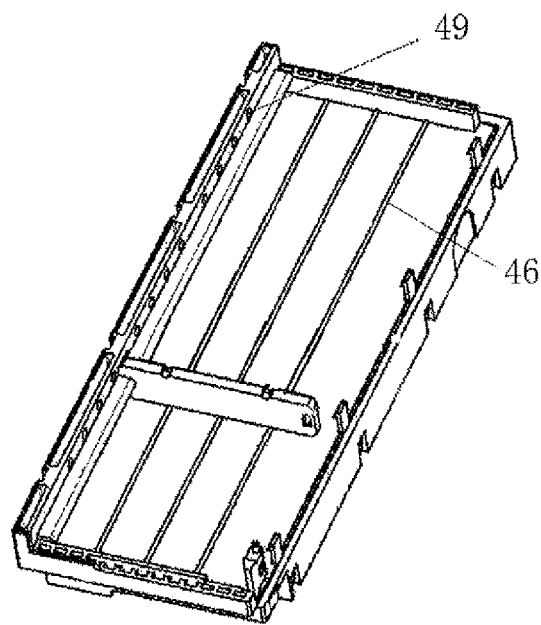
FIG. 11 is an internal structural schematic diagram of a reagent strip storage box.

As shown in FIG. 11, the reagent strip lowering guide rail 46 can be a guide rail attached to the inner wall of the body of the reagent strip storage box 32 or a guide rail suspended from the top, and the distance between the reagent strip lowering guide rail 46 and the bottom end of the reagent strip storage box 32 is between the thicknesses of 1-2 reagent strips.

As shown in FIG. 8, the reagent strip storage box bracket assembly 33 is provided with a sensor 50, through which the residual number of the reagent strips is counted.

In the fully-automatic immunofluorescence quantitative analyzing apparatus of the present embodiment, 3 reagent strip storage and automatic loading modules 3 are disposed and load 3 reagent strips every time. 16 cuvette ring reagent strip inserting slots 26 are disposed. The sample dispensing module 7 dispenses the sample to the reagent strip of Nth cuvette ring inserting slot, and the detection module 5 detects the reagent strip in the reagent strip inserting slot of the (N+13)th position. After the detection is finished, the position of the cuvette ring without the reagent strip rotates to an automatic loading region, and automatically loads the reagent strip into the cuvette ring by an elastic hook and begins a new loop.

In the embodiment, the loading process of the reagent strip is as follows:

the reagent strip is placed in the reagent strip storage box 32, in order to prevent an inaccurate test result caused by dampness of the reagent agent in the reagent strip storage box 32, drying agents are placed in the drying agent inserting holes 49 of the reagent strip storage box 32, and the reagent strip storage box 32 are sealed by inserting slots, screws, etc.

The reagent strip storage box 32 storing the reagent strip is placed in the inserting slot of the bracket assembly, the reagent box fixing padlock 34 is fastened to fix the reagent strip storage box 32.

By rotating the second motor 35 of the automatic popping out device, the second timing pulley 36 on the second motor 35 drives the second timing belt 37, such that the elastic hanging rod 38 is driven, the elastic hook 38 linearly moves on the reagent strip track 51 as shown in FIG. 47 and FIG. 11 by the notch 47 in the bottom of the reagent strip storage box 32, the reagent strip in the reagent strip storage box 32 is poked out by the sealing elastic piece 48, and the residual number of the reagent strips is counted by the sensor 50.

The reagent strip in the reagent strip storage box 32 can only move along the guide rail due to the action of the reagent strip lowering guide rail 46, and falls onto the bottom from the reagent strip storage box 32, thereby automatically loading the reagent strip.

Embodiment 3

According to the fully-automatic immunofluorescence quantitative analyzing apparatus, the detection module 5 is provided with an elastic hook, and other modules are structured similar to those of embodiment 2.

After the detection module 5 finishes the detection of the reagent strip, the elastic hook under the detection module 5 pushes the reagent strip out of the reaction disc, and the reagent strip enters to be under the detection device. After the detection of the next reagent strip is finished, the next reagent strip is pushed out of the device of the present embodiment by the last reagent strip, and the next reagent strip is kept below the detection device.

Embodiment 4

FIG. 13 shows a flow schematic diagram of a fully-automatic immunofluorescence quantitative analysis method, comprising the following steps:

step 1:) a reagent strip storage and automatic loading module loads a reagent strip to enter a reagent strip inserting slot of the cuvette ring;

step 2:) the cuvette ring starts to rotate, the reagent strip in a first position enters a sample dispensing region along with rotation and is paused, a sample in the sample module is sucked by the sample dispensing module to dispense into a reagent strip sample dispensing opening, and immunofluorescence reaction starts;

step 3:) the cuvette ring continuously rotates, the reagent strip in the first position gets away from the sample dispensing region, and the reagent strips in the subsequent position enter the sample dispensing region one after another, and are paused one by one, thus finishing sample dispensing;

step 4:) the cuvette ring continuously rotates, the reagent strip in the first position rotates to the detection module and is paused, and the detection device finishes the detection on the reagent strip in the first position and sends a result to a computer for processing.

The reagent strip loading method in the above method is to hook the reagent strip from the reagent strip storage box by the elastic handing rod with one elastic hook under the loading device.

In the analysis method of the present invention, the sample dispensing step comprises any one of the following two conditions:

A: condition in which the sample needs no diluting:) the sample dispensing device firstly picks a disposable sucker, then moves to a sample region to suck the sample, then moves to a cuvette ring region to finish a sample dispensing process, then moves to the recycling opening of a disposable tip collection box to remove the disposable sucker, and then performs a new round of sample dispensing;

B: the condition which the sample needs to be diluted:) the sample dispensing device firstly picks the disposable sucker, moves to the sample region to suck the sample, then moves to a diluent slot to dispense the sample into the diluent slot, then sucks diluent to inject, repeatedly sucks in and out to dilute the sample, then moves to the cuvette ring sample dispensing region to finish the sample dispensing, then recycles the disposable sucker, and then moves to a disposable tip box to pick a new sucker for a new round of sample dispensing.

In the analysis method of the present invention, various samples can be arrayed in the sample module, which is not limited in the present invention.

In the analysis method of the present invention, after the detection device detects the reagent strip, the elastic hook under the detection device pushes the reagent strip out of the cuvette ring to enter to be under the detection device, after the detection of the next reagent strip is finished, the last reagent strip is pushed out of the device of the present invention by the next reagent strip, and the next reagent strip is kept under the detection device. After the detection is finished, the cuvette ring without the reagent strip rotates to an automatic loading region, and the reagent strip is automatically loaded into the cuvette ring by the elastic hook to begin a new loop.

What is claimed is:

1. A fully-automatic immunofluorescence quantitative analyzing apparatus comprises:
   a support baseplate, a reagent strip storage and automatic loading module, a cuvette ring module, a detection module, a sample module, a sample dispensing module, a washing module and a control system, wherein the reagent strip storage and automatic loading module, the cuvette ring module, the detection module, the sample module, the sample dispensing module and the washing module are sequentially arranged on the support baseplate, wherein
   the reagent strip storage and automatic loading module provides a reagent strip for the cuvette ring module, the sample dispensing module dispenses the sample in the sample module to the cuvette ring module and performs a reaction, and the sample enters the detection module to complete the detection after the reaction is complete,
   the sample module comprises a disposable tip box, a mixing box, a diluent slot, a sample unit, a tip collection box and a sample module box;
   the sample unit and the diluent slot are located on a bottom plate of the sample module box, the bottom plate is provided with a track, the bottoms of the sample unit and the diluent slot are provided with a clamping slot matched with the track, and the sample unit and the diluent slot slide front and back on the track of the bottom plate, and
   one side of the sample module box is provided with a platform, the lower part of which is spaced from the ground, the tip collection box, the disposable tip box and the mixing box are arrayed on the platform, part of the tip collection box penetrates through the platform, on the platform, the other part of the tip collection box is in the spacing space of the lower part of the platform, the top end of the tip collection box is provided with a recycling opening, and the bottom end of the tip collection box is not sealed such that a disposable sucker directly falls onto the bottom plate after entering the recycling opening.

2. The immunofluorescence quantitative analyzing apparatus according to claim 1, wherein
   the sample dispensing module comprises an XYZ motion mechanical arm, a disposable tip detector, and a diluter pump,
   the XYZ motion mechanism arm comprises an X arm, a Y arm and a Z arm, and the X arm is horizontally disposed along the sample module and the cuvette ring module;
   the Y arm is located on the upper part of the sample module, is vertically connected to the X and can slide on the X arm, and
   the Z arm is vertically fixed in a chute of the Y arm, the bottom of the Z arm is provided with the disposable tip detector, the diluter pump is connected to the disposable tip detector and provides sampling power for the disposable tip detector.

3. The immunofluorescence quantitative analyzing apparatus according to claim 1, wherein the sample module box is set to be a drawer shape, baffles are disposed on left and right sides, pulleys are disposed outside the baffles and can slide front and back along outside slideways, and the front ends of the baffles are provided with fixed bolts for fixing the drawer.

4. The immunofluorescence quantitative analyzing apparatus according to claim 1, wherein
   the cuvette ring module is a disc-like device, reagent strip inserting slots are fixed on the edge of the disc, and inserting slot openings correspond to a reagent strip outlet of the reagent strip storage and automatic loading module in position to load the reagent strip,
   the cuvette ring brings the reagent strip to the position corresponding to the sample dispensing module to finish the sample dispensing operation, and
   the cuvette ring brings the reagent strip to the position corresponding to the detection module to finish detection operation.

5. The immunofluorescence quantitative analyzing apparatus according to claim 4, wherein
   the cuvette ring is connected to a first motor, and the first motor drives the cuvette ring to rotate by driving a first timing pulley and a first timing belt, and
   a number of the cuvette ring reagent strip inserting slots is 2N or 2N+1, and N is larger than or equal to 1.

6. The immunofluorescence quantitative analyzing apparatus according to claim 1, wherein
   the reagent storage and automatic loading module comprises a reagent strip storage box, a storage box bracket and an automatic loading assembly, the storage box bracket is fixed on the support baseplate, and the reagent strip storage box is fixed on the storage box bracket by a padlock,
   the automatic loading assembly consists of a second motor, a second timing pulley, a second timing belt, and an elastic hanging rods,
   the control system controls the second motor to operate and drives the second timing pulley, the second timing belt, and the elastic hanging rod to move, and
   a reagent strip inserting slot is disposed in the cuvette ring module, the lower bottom surface is provided with a notch, and the notch allows the elastic hanging rod to feed the reagent strip to enter the reagent strip inserting slot.

7. The immunofluorescence quantitative analyzing apparatus according to claim 6, wherein
   the reagent strip storage box comprises a box body and a box cover part, which are sealed,
   a reagent strip lowering guide rail is in the reagent strip storage box; the bottom of the reagent strip storage box is provided with a notch, and a sealing elastic piece is disposed on the bottom end of the side surface of the reagent strip storage box close to the notch, and 1-3 reagent strip storage and automatic loading modules are disposed.

8. The immunofluorescence quantitative analyzing apparatus according to claim 1, wherein the washing module comprises a probe washing slot, a waste liquid bottle, and a washing liquid bottle, wherein a catheter in the probe washing slot is connected to the waste liquid bottle and the washing liquid bottle.

9. A detection method of the fully-automatic immunofluorescence quantitative analyzing apparatus according to claim 1, comprising the following steps:
step 1: a reagent strip storage and automatic loading module loads a reagent strip to enter a reagent strip inserting slot of the reaction disc;
step 2: a cuvette ring starts to rotate, the reagent strip in a first position enters a sample dispensing region along with rotation and is paused, a sample in the sample module is sucked by the sample dispensing module to dispense into a reagent strip sample dispensing opening, and immunofluorescence reaction starts;
step 3: the cuvette ring continuously rotates, the reagent strip in the first position gets away from the sample dispensing region, and the reagent strips in the subsequent position enter the sample dispensing region one after another, and are paused one by one, thus finishing sample dispensing; and
step 4: the cuvette ring continuously rotates, the reagent strip in the first position rotates to the detection module and is paused, and the detection device finishes the detection on the reagent strip in the first position and sends a result to a computer for processing.

10. The detection method according to claim 9, wherein, the sample dispensing step comprises either one of the following two conditions:
A: a condition in which the sample needs no diluting: the sample dispensing device firstly picks the disposable sucker, then moves to a sample region to suck the sample, then moves to a cuvette ring region to finish a sample dispensing process, then moves to the recycling opening of a disposable tip collection box to remove the disposable sucker, and then performs a new round of sample dispensing; and
B: a condition which the sample needs to be diluted: the sample dispensing device firstly picks the disposable sucker, moves to the sample region to suck the sample, then moves to a diluent slot to dispense the sample into the diluent slot, then sucks diluent to inject, repeatedly sucks in and out to dilute the sample, then moves to the cuvette ring sample dispensing region to finish the sample dispensing, then recycles the disposable sucker, and then moves to a disposable tip box to pick a new sucker for a new round of sample dispensing.

11. A fully-automatic immunofluorescence quantitative analyzing apparatus comprises:
a support baseplate, a reagent strip storage and automatic loading module, a cuvette ring module, a detection module, a sample module, a sample dispensing module, a washing module and a control system, wherein the reagent strip storage and automatic loading module, the cuvette ring module, the detection module, the sample module, the sample dispensing module and the washing module are sequentially arranged on the support baseplate, wherein
the reagent strip storage and automatic loading module provides a reagent strip for the cuvette ring module, the sample dispensing module dispenses the sample in the sample module to the cuvette ring module and performs a reaction, and the sample enters the detection module to complete the detection after the reaction is complete,
the reagent storage and automatic loading module comprises a reagent strip storage box, a storage box bracket and an automatic loading assembly, the storage box bracket is fixed on the support baseplate, and the reagent strip storage box is fixed on the storage box bracket by a padlock,
the automatic loading assembly consists of a second motor, a second timing pulley, a second timing belt, and an elastic hanging rod,
the control system controls the second motor to operate and drives the second timing pulley, the second timing belt, and the elastic hanging rod to move, and
a reagent strip inserting slot is disposed in the cuvette ring module, the lower bottom surface is provided with a notch, and the notch allows the elastic hanging rod to feed the reagent strip to enter the reagent strip inserting slot.

12. The immunofluorescence quantitative analyzing apparatus according to claim 11, wherein
the sample dispensing module comprises an XYZ motion mechanical arm, a disposable tip detector, and a diluter pump,
the XYZ motion mechanism arm comprises an X arm, a Y arm and a Z arm, and the X arm is horizontally disposed along the sample module and the cuvette ring module;
the Y arm is located on the upper part of the sample module, is vertically connected to the X and can slide on the X arm, and
the Z arm is vertically fixed in a chute of the Y arm, the bottom of the Z arm is provided with the disposable tip detector, the diluter pump is connected to the disposable tip detector and provides sampling power for the disposable tip detector.

13. The immunofluorescence quantitative analyzing apparatus according to claim 11, wherein
the cuvette ring module is a disc-like device, reagent strip inserting slots are fixed on the edge of the disc, and inserting slot openings correspond to a reagent strip outlet of the reagent strip storage and automatic loading module in position to load the reagent strip,
the cuvette ring brings the reagent strip to the position corresponding to the sample dispensing module to finish the sample dispensing operation, and
the cuvette ring brings the reagent strip to the position corresponding to the detection module to finish detection operation.

14. The immunofluorescence quantitative analyzing apparatus according to claim 13, wherein
the cuvette ring is connected to a first motor, and the first motor drives the cuvette ring to rotate by driving a first timing pulley and a first timing belt, and
a number of the cuvette ring reagent strip inserting slots is 2N or 2N+1, and N is larger than or equal to 1.

15. The immunofluorescence quantitative analyzing apparatus according to claim 11, wherein
the reagent strip storage box comprises a box body and a box cover part, which are sealed,
a reagent strip lowering guide rail is in the reagent strip storage box; the bottom of the reagent strip storage box is provided with a notch, and a sealing elastic piece is disposed on the bottom end of the side surface of the reagent strip storage box close to the notch, and
1-3 reagent strip storage and automatic loading modules are disposed.

16. The immunofluorescence quantitative analyzing apparatus according to claim 11, wherein the washing module comprises a probe washing slot, a waste liquid bottle, and a washing liquid bottle, wherein a catheter in the probe washing slot is connected to the waste liquid bottle and the washing liquid bottle.

17. A detection method of the fully-automatic immunofluorescence quantitative analyzing apparatus according to claim 11, comprising the following steps:

step 1: a reagent strip storage and automatic loading module loads a reagent strip to enter a reagent strip inserting slot of the reaction disc;

step 2: a cuvette ring starts to rotate, the reagent strip in a first position enters a sample dispensing region along with rotation and is paused, a sample in the sample module is sucked by the sample dispensing module to dispense into a reagent strip sample dispensing opening, and immunofluorescence reaction starts;

step 3: the cuvette ring continuously rotates, the reagent strip in the first position gets away from the sample dispensing region, and the reagent strips in the subsequent position enter the sample dispensing region one after another, and are paused one by one, thus finishing sample dispensing; and step 4: the cuvette ring continuously rotates, the reagent strip in the first position rotates to the detection module and is paused, and the detection device finishes the detection on the reagent strip in the first position and sends a result to a computer for processing.

18. The detection method according to claim 17, wherein, the sample dispensing step comprises either one of the following two conditions:

A: a condition in which the sample needs no diluting: the sample dispensing device firstly picks a disposable sucker, then moves to a sample region to suck the sample, then moves to a cuvette ring region to finish a sample dispensing process, then moves to the recycling opening of a disposable tip collection box to remove the disposable sucker, and then performs a new round of sample dispensing; and B: a condition which the sample needs to be diluted: the sample dispensing device firstly picks the disposable sucker, moves to the sample region to suck the sample, then moves to a diluent slot to dispense the sample into the diluent slot, then sucks diluent to inject, repeatedly sucks in and out to dilute the sample, then moves to the cuvette ring sample dispensing region to finish the sample dispensing, then recycles the disposable sucker, and then moves to a disposable tip box to pick a new sucker for a new round of sample dispensing.

* * * * *